United States Patent [19]

Longhenry

[11] 3,942,899

[45] Mar. 9, 1976

[54] CALIBRATING DEVICE FOR LIGHT SCATTER PHOTOMETERING INSTRUMENT

[75] Inventor: David K. Longhenry, East Lyme, Conn.

[73] Assignee: Pfizer, Inc., New York, N.Y.

[22] Filed: Feb. 4, 1975

[21] Appl. No.: 547,012

Related U.S. Application Data

[63] Continuation of Ser. No. 371,389, June 19, 1973, Pat. No. 3,901,588.

[52] U.S. Cl. ................. 356/234; 356/244; 356/103

[51] Int. Cl.[2] ...................... G01J 1/40; G01N 21/06

[58] Field of Search ............. 356/234, 235, 244, 81, 356/103, 224, 225; 350/314, 318, 315, 316

[56] References Cited

UNITED STATES PATENTS

| | | | |
|---|---|---|---|
| 1,419,725 | 6/1922 | Fisher | 350/314 |
| 2,244,507 | 6/1941 | Thomas | 350/314 |
| 2,682,801 | 6/1954 | Davidson et al. | 350/314 |
| 3,381,572 | 7/1968 | Tvwiner | 350/314 |
| 3,418,484 | 12/1968 | Harmon | 350/314 |
| 3,627,424 | 12/1971 | Dorman et al. | 356/103 |
| 3,832,532 | 8/1974 | Praglin et al. | 356/81 |

*Primary Examiner*—Alfred E. Smith
*Assistant Examiner*—Jon W. Henry
*Attorney, Agent, or Firm*—Connolly and Hutz

[57] ABSTRACT

A flat sandwich composite plate of nested wedge-shaped sheets of highly transparent and gray neutral density filter glasses is enclosed in a frame. A bracket on the frame mounts it on the carriage of an optical instrument which measures the light scattering characteristics of a series of samples traversed on a carriage past a photometering station. A surface of the composite plate has a mat finish which scatters the light passing through it. The density and thickness of the filter glass are arranged to cover a predetermined range of light scatter corresponding to that caused by the range of samples which the optical instrument can accurately measure. An appended flat section of filter glass provides light scatter characteristics corresponding to an auxiliary sample characteristic. The transmittance of the appended section is adjusted by a movable leaf and notched adjusting segments. The mat surface is obtained by frosting a surface of the filter glass by blasting or grinding with 9 micron grit. The neutral density filter glass has a flat spectrum characteristic obtained by doping with carbon.

5 Claims, 10 Drawing Figures

66
22
68
81
87
72
62
70
RUN
RESET
READY
DOOR
TEST
LAMP
STAND.
CUVETTE
79
STAND.
89
PAPER
2
75
92
74
80
88
94
86
12
46
102
104
44
86
84
108
77
67
62a
62b
2

78
80
92
90
91
220
46
200
86
86
222
236
88
226
204
44
88
202
206
94
108
224
228
82
76
44
102
104
106
96
97

CALIBRATING DEVICE FOR LIGHT SCATTER PHOTOMETERING INSTRUMENT

Cross-Reference to Related Application

This is a continuation of U.S. Pat. application Ser. No. 371,389, filed June 19, 1973, now U.S. Pat. No. 3,901,588.

BACKGROUND OF THE INVENTION

A method and apparatus for testing antibiotic susceptibility by measuring the forward light scattering of a series of samples containing standard and test samples of bacteria colonies affected by various antibiotic elutions is described in commonly assigned patent application Ser. No. 281,946, filed Aug. 18, 1972 now U.S. Pat. No. 3,832,532 A photometering analyzer measures the light scattering characteristics of each of a series of samples traversed on a carriage past a photodetecting station. The analyzer prints out a range of readings indicative of the characteristic being measured. The analyzer also provides a reading of a preliminary sample concentration, which is also obtained by light scattering. This analyzer includes various optical and electronic components which would cause erroneous readings if any or some of them should malfunction. An object of this invention is to provide a means for readily determining if such a light scattering photometering analyzer is accurately functioning.

SUMMARY

In accordance with this invention, a calibrating standard for an optical instrument, which measures the light scattering characteristics of a series of samples traversed on a carriage past a photometering station, includes an elongated framed flat sandwich plate of nested wedge-shaped sheets of highly transparent and gray neutral density filter glasses. A surface of the composite plate has a mat finish which scatters the light passing through it. The density and thickness of the filter glass are arranged to cover a predetermined range of light scatter corresponding to that caused by a predetermined range of samples which the optical instrument is capable of measuring. Traversal of the plate in a series of steps over its length past the photometering station provides a series of readings which can be compared with a standard set of readings obtained by an accurately functioning standard instrument to determine whether the instrument being calibrated is functioning accurately over its entire range. An appended flat section of neutral filter glass in line with the filter wedge is used to verify whether a preliminary light scattering reading is being accurately determined. The neutral density filter glass having a flat spectrum characteristic obtained by doping an otherwise highly transparent glass with carbon. The reading obtained from the appended section may be varied by adjusting the position of a superimposed leaf.

BRIEF DESCRIPTION OF THE DRAWINGS

Novel features and advantages of the present invention will become apparent to one skilled in the art from a reading of the following description in conjunction with the accompanying drawings wherein similar reference characters refer to similar parts and in which.

DESCRIPTION OF THE PREFERRED EMBODIMENT

Figure 1:
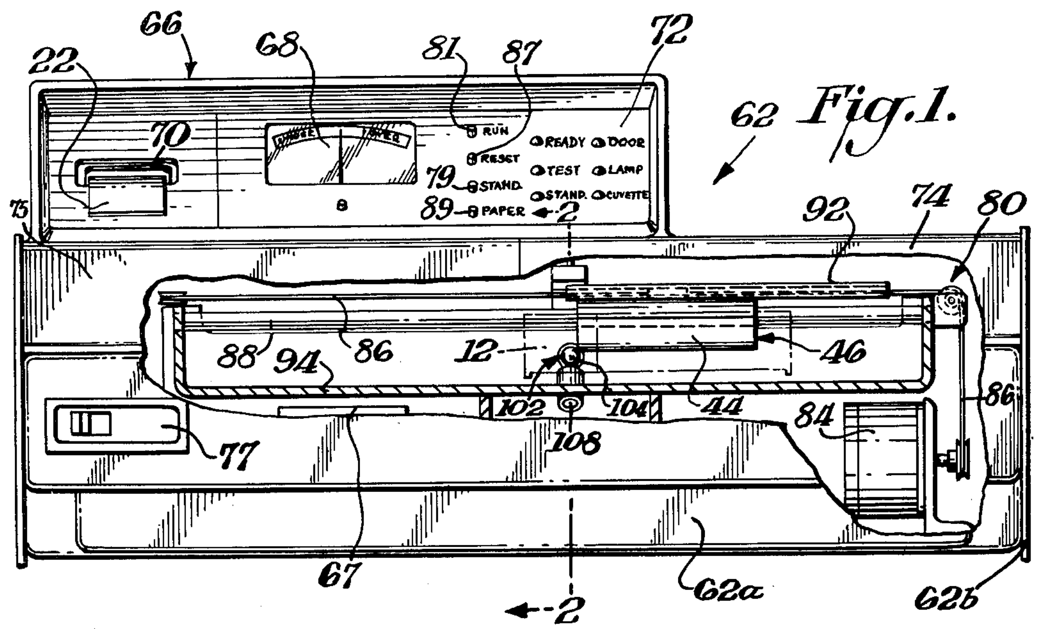
FIG. 1 is a front view in elevation partially broken away and partially in cross-section of an analyzer with a sample container for which an embodiment of this invention is substututed to calibrate the analyzer.
Figure 2:
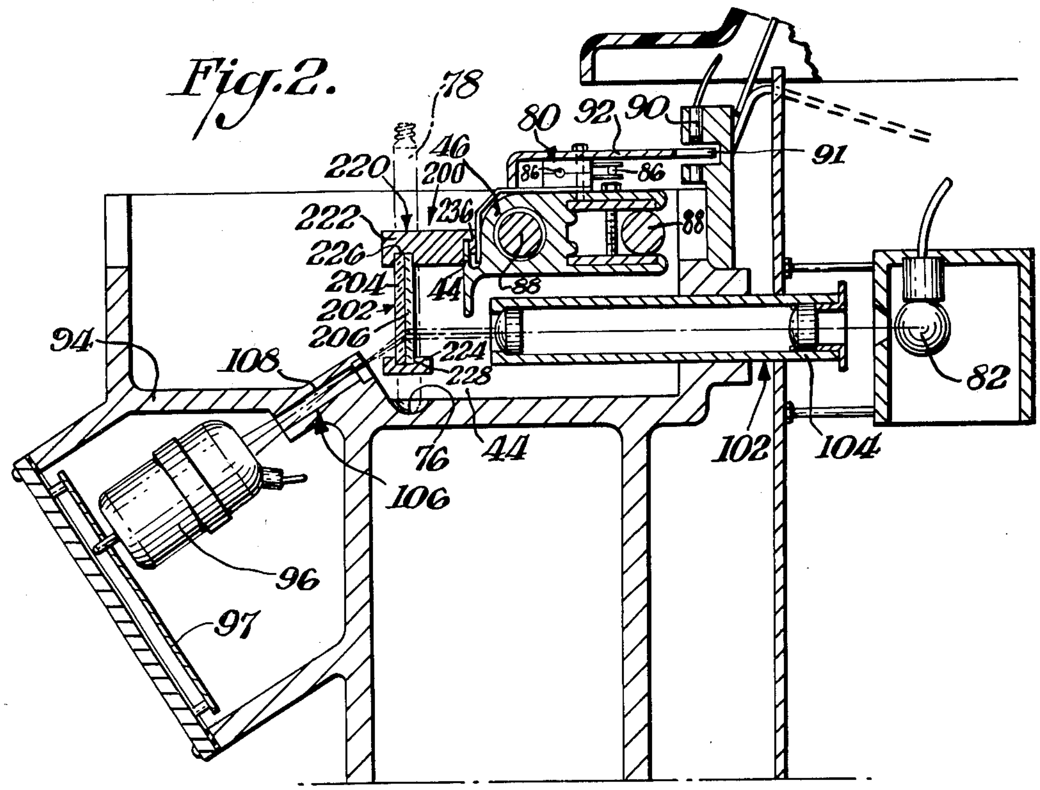
FIG. 2 is a cross-sectional side elevational view taken through FIG. 1 along the line 2—2 with the calibrating device of this invention substituted for the sample container shown in FIG. 1.

FIGS. 1 and 2 show portions of photometer analyzer 62, which is fully described in the aforementioned copending patent application, and whose operation is verified by calibrating device 200 which is shown in analyzer 62 in FIG. 2 and individually in FIGS. 5–10. Photometer and analyzer 62 has three principal functions:

1. inoculum standarization to provide the means for determining when the microbial concentration of the starting saline stock inoculum is within relatively narrow and well defined limits (e.g., 1 to $2\times10^7$ cells/milliliter); (2) to provide the means for determining the level of growth in all scattering chambers of the incubated cuvette; and (3) to calculate and print out for each scattering chamber containing an antimicrobial, a reading which is readily interpretable in terms of the susceptibility or resistance of the microorganism to the antimicrobial agent. Calibrating device 200 verifies the accurate performance of all of these functions.

FIG. 1 shows a front view of the instrument 62 with doors 74 and 75 closed. The control panel 66 wih the inoculum meter 68 and printer slot 70 is contained in instrument housing 72. The doors 74 and 75 give access to cuvette carriage 46. A port (not shown) in the right door 74 is provided for inserting inoculum tube 78 (shown in phantom outline in FIG. 2) with its lower and resting within indentation 76 in casting 94. Normally only the right door 74 is open. The left door 75 is provided for maintenance purposes. On the left side below the door 75 is the instrument power switch 77. Instrument cover 66 and instrument front 62*a* are fabricated from 5/32 inch ABS plastic while the doors 74, 75 and front panel 72 and frame 62*b* are steel or aluminum.

Figures 3, 4, 5, 6, 7, 8, 9, 10:
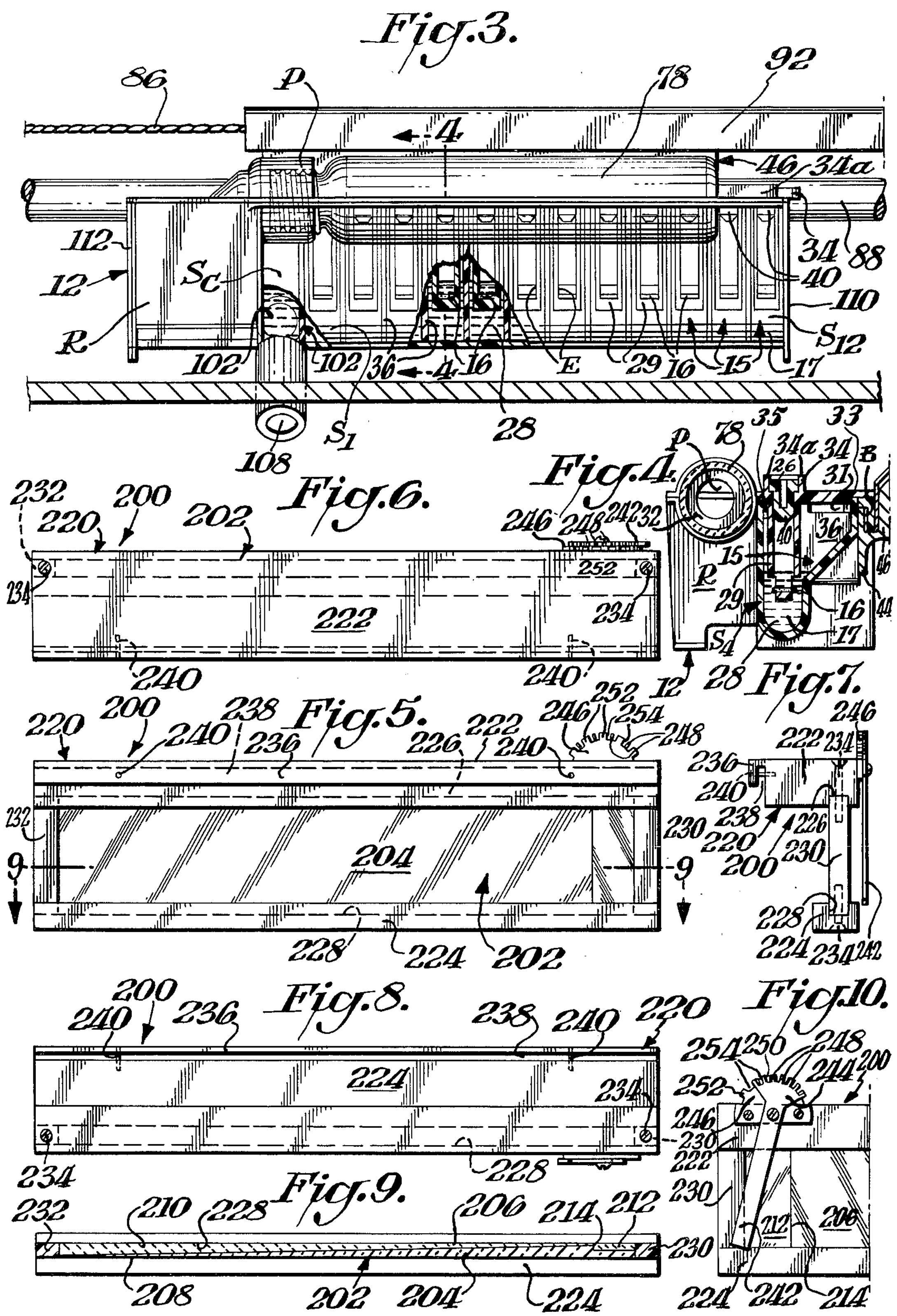
FIG. 3 is an enlarged front view in elevation partially in cross-section of the sample container mounted in a portion of the analyzer shown in FIG. 1.
FIG. 4 is a cross-sectional view taken through FIG. 3 along the line 4—4.
FIG. 5 is a rear view in elevation of the embodiment of this invention shown in FIG. 2 installed in the analyzer.
FIG. 6 is a top plan view of the embodiment shown in FIG. 5.
FIG. 7 is a right-hand end view of the embodiment shown in FIG. 5.
FIG. 8 is a bottom plan view of the embodiment shown in FIG. 5.
FIG. 9 is a cross-sectional view taken through FIG. 5 along the line 9—9.
FIG. 10 is a front elevational view of the reverse of the right-hand side of the embodiment shown in FIG. 5.

FIGS. 1, 3 and 4 show instrument 62 with cuvette 12 in place. Cuvette drive mechanism 80 (shown in FIG. 2) traverses cuvette 12 from right to left past photometer light source 82 and the optical system 102. This mechanism employs a motor 84 linked via a cable 86 to carriage 46 sliding on parallel bars 88. Limit switches (not shown) actuate forward or reversing movement of motor 84. An optical sensor 90 on the instrument senses the cuvette position by reading index slots 91 in a slide 92 mounted on carriage 46.

FIG. 1 shows instrument 62 from the front with covers broken away. Transformer 67 is on the lower left and drive motor 84 is on the right. In the center is the main casting 94 which holds the drive mechanism 80. The photometer transducer 96(shown in FIG. 2) is in its base.

FIG. 2 shows light source 82 and optical system 102. Optical system 102 employs a Quartz Halogen lamp 82 and a simple two lens condensing system 104. Receiver 106 uses a collimator tube 108 placed at a 35° angle. A photometer transducer 96 includes a photo cell circuit of any functional type. Printed circuit cards (not shown) comprise the control and regulator electronic section of this device. Printed circuit cards (also not shown) comprise the calculating and computing section of this device.

The standard inoculum is a suspension of a pure bacteria in 0.90 gm % sodium chloride which is between the limits of 1 to $2\times10^7$ viable cells per milliliter. This standard saline stock inoculum in an optically acceptable (i.e., clean, scratch-free) 16×125 mm round-bottom flint glass tube 78 will give a 35° angle scattering signal of −log S between 2.2. ($1\times10^7$ cells per ml.) and 1.9 ($2\times10^7$ cells/ml) when placed in the photometer. The photometerstandardization meter 68 has a central region (occupying 40 percent of the total meter range) stating "Correst Inoculum Range." Its two boundaries correspond to the two acceptable scattering limits. The left region of the meter (occupying 30 percent of the total meter range) states "Under" and/or "Add More Organisms", while the right region (occupying the remaining 30 percent of the total meter range) states "Over" and/or "Dilute With Saline." The accurate functioning of the meter is verified by flat filter element 212 as later described.

Cuvette 12 is shown in FIG. 1 being traversed on carriage 46 past photometering station or optical system 102. Cuvette 12 is a container for inoculated broth in which the effect of antimicrobial agents on the growth of microorganisms in the broth is measured. The detection of growth in broth by forward light scattering requires such a chamber to be both optically transparent to the irradiating light used and geometrically consistent with the light scattering photometer. Convenient and rapid examination of the effect of many antimicrobial agents on the growth of a given microorganism is accomplished by a linear array of such optical chambers as a single unit. Cuvette 12 also permits the convenient introduction of an equal volume of broth inoculum into each chamber S. Cuvette 12 also has the capability of conveniently accepting an antimicrobial impregnated paper disc into all test chambers and is not capable of accepting such an antimicrobial disc in its single control chamber. Furthermore, cuvette 12 is water-tight, optically polished, optically reproducible, inexpensive, relatively small, stackable, and may be disposable.

Cuvette 12 is shown in FIGS. 1, 3 and 4. It is composed of optically clear and inert plastic, such as polystyrene, and is produced by the injection molding process in two sections using optically polished steel molds. After injection molding, the two sections are sealed together by either solvent or ultrasonic energy to produce the cuvette. Ultrasonic sealing is preferable because it avoids marring of the optical surface by excess solvent. Cuvette 12 is a linear array of one control chamber, $S_c$, and twelve antimicrobial test chambers, $S_{1\text{-}12}$. The only other material besides polystyrene used in the illustrated cuvette 12 is a flexible polymer, such as Krayton. Krayton is the trademark for a styrene-butadiene polymer made and sold by The Shell Chemical Co. Krayton gasket 32 and a closure 34 are inserted into cuvette 12 prior to final packaging.

Cuvette 12 includes six main parts:

1. Inoculum tube port (P) which accepts inoculum tube 78;
2. Reservoir (R);
3. Interconnected Distributing Lobes 15, connected to the reservoir by a major distribution port 31, distributing ports 33, and vents 35;
4. Light Scattering Lobes 17: Thirteen disconnected light scattering lobes 17 of chambers $S_c$, ($S_1$, $S_2$. . . $S_{12}$) accept an equal volume of broth inoculum from interconnected distributing lobes 15;
5. Tubular Antimicrobial Disc Holders (29): Each hollow finger, also referred to as a disc holder, accepts an antimicrobial paper disc 16 (6.5 mm diameter) via twelve disc ports 26 on the top surface of cuvette 12. Two elution ports, E, in the walls of the disc holder adjacent to the disc permit elution of antimicrobial agent into the surrounding broth inoculum of the scattering chamber. Sealing strip 34 with nipples 40 inserted in ports 26 is received between parallel rails **34*a* straddling ports 26 on the upper surface of cuvette 12.**
6. Bracket B: An L-shaped bracket B located on the back of cuvette 12 and extending the length of the cuvette long axis enables the attachment of the cuvette to the holding bracket 44 of the photometer carriage 46.

In FIG. 2 calibrating standard 200 is shown installed in analyzer 62 for traversal past the photometering station provided by optical system 102. Details of calibrating device 200 are shown in FIGS. 5–10. Calibrating device 200 includes an elongated composite glass plate 202 comprising a flat sandwich of nested wedge-shaped sheets of highly transparent glass 204 and gray neutral density filter glass 206 which are firmly adhered to each other to provide substantially parallel clear glass and filter glass outer surfaces 208 and 210. A flat section 212 of gray neutral density filter glass is appended to the thin edge 214 of filter wedge 206 opposite a correspondingly flat step 216 in the clear glass adjacent the thicker edge of clear glass wedge 204.

The overall thickness of composite plate 202 is about 0.217 inch. This edge 214 of filter glass wedge 206 is approximately 0.010 inch thick and the opposite thin edge 218 of clear glass wedge 204 is about 0.060 inch thick. Flat section 212 of filter glass is about ½ inch wide and about 0.100 inch thick. Neutral density filter glass in wedge 206 and section 212 is for example obtained by doping a highly transparent optical glass with carbon to reduce its light transmitting capability. This provides a filter having a substantially flat spectrum of light transmission over its range of light absorption. Surface 210 of the filter glass has a mat finish to diffuse or scatter the light passing through plate 202. This mat finish is for example obtained by frosting the surface of the filter glass by polishing or blasting with 9 micron grit of HF acid etching.

Plate 202 is mounted in an elongated frame 220 made for example of aluminum anodized black to prevent light reflection. Frame 220 includes top horizontal channel section 222 and bottom horizontal channel section 224 respectively containing upper groove 226 and lower groove 228 which receive the top and bottom edges of plate 202. Channel sections 222 and 224 are secured together by end rods 230 and 232 secured to channels 222 and 224 by countersunk flat-headed screws 234.

Top channel section 222 is rearwardly extended to provide a hanger portion 236 including groove 238 which is hooked over bracket 44 on carriage 46 to mount calibrating device 200 in analyzer 62 as shown in FIG. 2. Pins 240 through hanger portion 236 and grooves 238 laterally locate calibrating device 220 on bracket 44 for accurate and consistent traversal past optical system 102.

Variable leaf 242 is rotatably mounted in front of flat filter section 212 for adjusting the amount of light passing through it to the photometering device. Leaf 242 has an arcuate upper section 244 mounted over a hemispherical adjusting plate 246 attached to the front of upper channel section 222. Arcuate section 244 has a series of equally spaced teeth 248 and notches 250 disposed in front of corresponding teeth 252 and slightly larger notches 254 in a hemispherical plate 246. The position of leaf 242 in front of flat filter section 212 may be adjusted by inserting and twisting a flat blade within a pair of adjacent notches 250 and 254. The amount of scattering light passing through flat filter section 212 may accordingly be adjusted to a standard reading by adjusting the position of leaf 242. This permits the preliminary auxiliary sample reading of the instrument to be verified to make sure that a standard reading is obtained corresponding to the standard scattering obtained by the proper concentration of the predetermined concentration of colonies of a given bacteria in a standard inoculum. This concentration reading is the inoculum standardization function of analyzer 62 shown in FIG. 2 with inoculum tube 78 (phantom outline) exposed to optical system 102 and read on standardization meter 68.

The major or wedge-shaped portions of calibrating device 200 are utilized for verifying the remaining primary functions of analyzer 62 of determining the level of microbial growth in the scattering chambers of cuvette 12 and printing out readings indicative of the susceptibility of resistance of the microorganism to particular antimocrobial agents. This is accomplished by installing device 200 in instrument 62 as shown in FIG. 2. Analyzer 62 is then actuated to step device 200 past optical system 102 in a series of stations corresponding to the positions of sample specimen containers or chambers $S_{1-12}$ of cuvette 12. This provides a series of readings, for example on a print-out sheet, which should cover the predetermined range of light scatter corresponding to those provided by the range of bacteria growth occurring in chambers $S_{1-12}$ of cuvette 12. The set of readings is then compared with a standard set of readings, formerly obtained in a standard calibrated instrument 62 by calibrating device 200. These readings should also have a linear relationship as a result of the wedge shape of filter section 206. As long as the readings obtained by the transversal of calibrating device 200 past optical system 102 are within a predetermined range of tolerance, such as 2 percent, analyzer 62 is in proper operating condition.

I claim:

1. An optical instrument comprised of a carriage with means for carrying a plurality of samples and means for moving said carriage past a photometering station for measuring the light scattering characteristics of said series of samples traversed on said carriage in steps past said photometering station in combination with a device for calibrating said optical instrument, an elongated frame, a bracket attached to the frame readily detachably mounting said frame upon said carriage in a predetermined position, an elongated composite plate of transparent glass in said frame, said composite plate comprising a flat sandwich of nested wedge-shaped sheets of highly transparent and neutral density filter glasses, a surface of said composite plate having a uniform mat finish which scatters the light passing through it, and the density of the filter glass being sufficient to cover a predetermined range of light scatter corresponding to that caused by a predetermined range of said samples throughout the varying thickness of said filter glass over the length of said composite plate as said device is traversed in steps past the photometering station.

2. A device as set forth in claim 1, wherein said mat finish comprises a frosted surface.

3. A device as set forth in claim 2 wherein said frosted surface has irregularities and said irregularities are about a 9 micron size.

4. A device as set forth in claim 1 wherein said wedge-shaped sheets have substantially blunt edges from about 0.060 inch to about 0.010 inch thick.

5. A device as set forth in claim 1 wherein said neutral density filter glass is a gray flat spectrum neutral density filter glass incorporating carbon.

* * * * *